United States Patent [19]
Astarita

[11] Patent Number: 5,662,613
[45] Date of Patent: Sep. 2, 1997

[54] ENDOSCOPIC INSTRUMENT LOCK

[76] Inventor: Denis C. Astarita, 801 N. Tustin Ave., Ste. #305, Santa Ana, Calif. 92705

[21] Appl. No.: 649,118

[22] Filed: May 14, 1996

[51] Int. Cl.⁶ .................................................. A61M 5/00
[52] U.S. Cl. ........................................ 604/165; 604/170
[58] Field of Search ................................. 604/164, 165, 604/170, 158

[56] References Cited

U.S. PATENT DOCUMENTS

| | | | |
|---|---|---|---|
| 4,122,836 | 10/1978 | Burnett | 128/1.1 |
| 4,414,974 | 11/1983 | Dotson | 128/305 |
| 4,863,430 | 9/1989 | Klyle | 604/170 |
| 5,057,085 | 10/1991 | Kopans | 604/158 |
| 5,135,502 | 8/1992 | Koenig, Jr. | 604/165 |
| 5,256,149 | 10/1993 | Banik et al. | |
| 5,312,375 | 5/1994 | Gurmarnik | 604/158 |
| 5,330,492 | 7/1994 | Haugen | 606/167 |
| 5,545,200 | 8/1996 | West | 607/122 |

FOREIGN PATENT DOCUMENTS

| | | | |
|---|---|---|---|
| 0605067 | 5/1926 | France | 604/165 |
| 0123520 | 8/1919 | United Kingdom | 604/165 |

Primary Examiner—Sam Rimell
Assistant Examiner—Luke J. Yeh
Attorney, Agent, or Firm—James G. O'Neill

[57] ABSTRACT

A locking device for use in a trocar inserted into a body cavity. The locking device includes an enlarged head that may be easily grasped and recognized by a surgeon during complicated surgery and an elongated shaft portion secured to the enlarged head, which is conformable to a gas opening in the trocar for quick and easy insertion into the gas opening, by turning the enlarged head. The locking device has coarse self-tapping threads formed only on an upper portion of the elongated shaft, adjacent to the enlarged head to enable the locking device to be quickly turned into a locking position for any type of instrument passing through the trocar into the body cavity. The outer and of the elongated shaft contacting the instrument must be blunt and soft to prevent damaging or marring the instrument against which it is pressed.

16 Claims, 1 Drawing Sheet

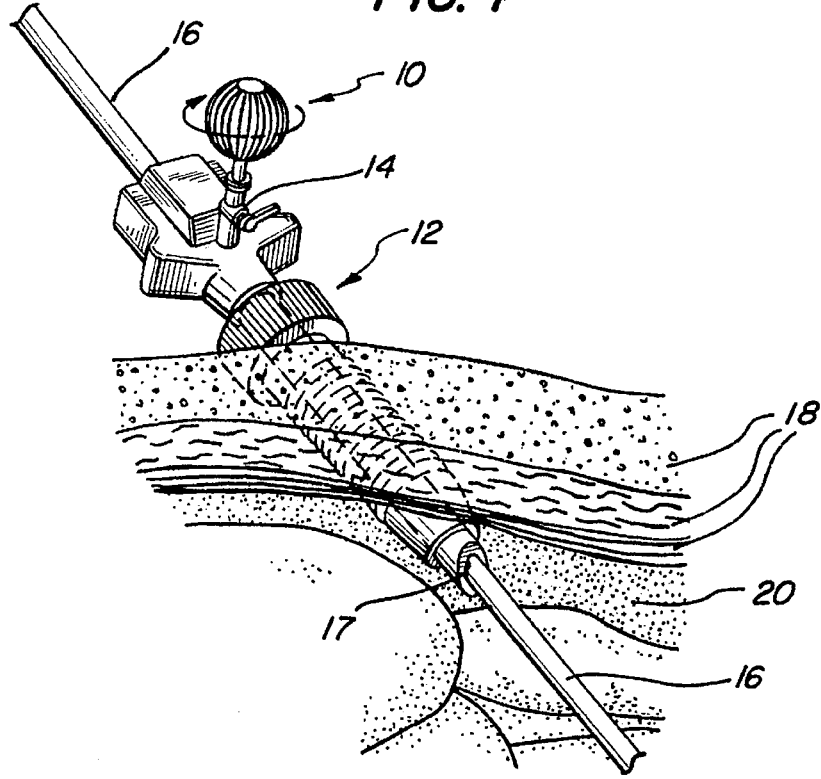
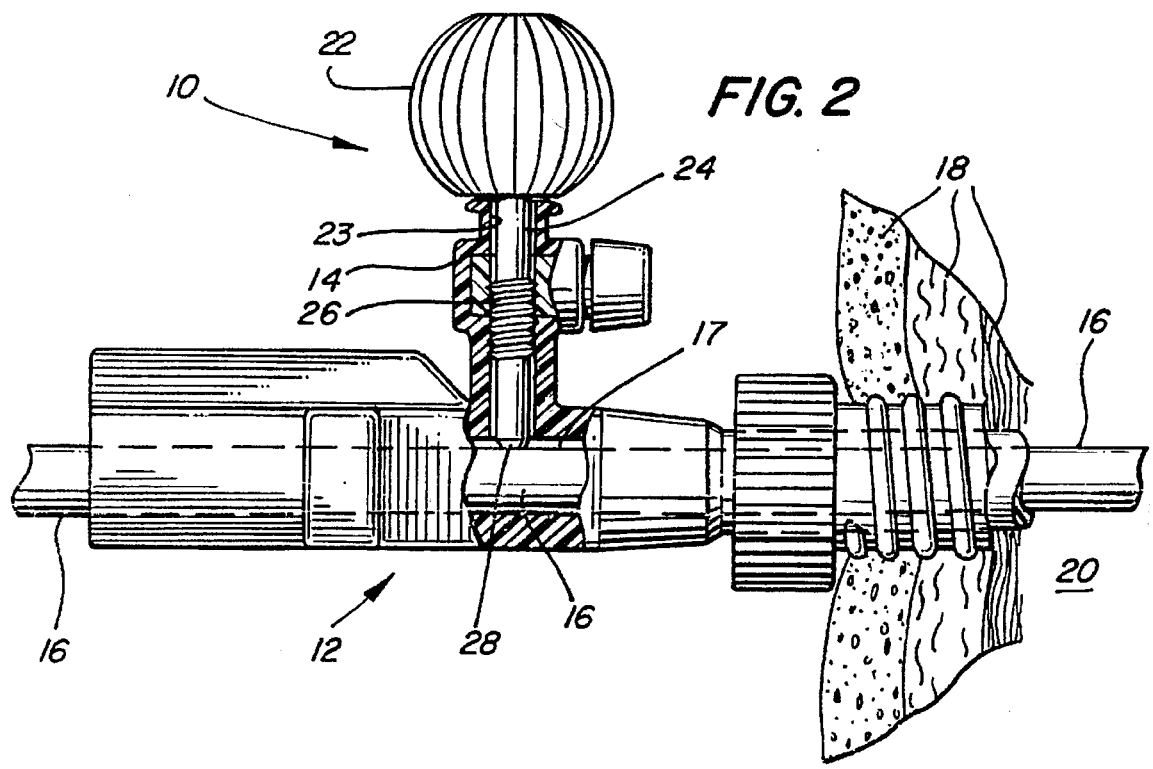

ENDOSCOPIC INSTRUMENT LOCK

BACKGROUND OF THE INVENTION

1. Field of the Invention

This invention relates generally to trocars for use in endoscopic surgery and, more particularly, to a locking device for easy insertion into and removal from an existing opening in a trocar, and for securing an instrument inserted through the trocar into a body cavity in position so as to prevent movement thereof.

2. Description of Related Art

As is well known, surgical devices, such as trocars are widely used in endoscopic surgery. Trocars are devices that are used to provide access to a surgical site within a patient's body cavities. A trocar is typically inserted through a small skin incision by pressing the distal end of the trocar against the outer skin of the patient with sufficient force applied to the trocar handle so that the piercing tip of an obturator effectively penetrates the patient's skin and underlying fat tissue, fascia, muscle and into a selected internal cavity. The trocar obturator is removed and the trocar cannula is then used as a passageway to and from the patient's body cavity. During many procedures a number of trocars are required so that a number of passageways are formed into the selected body cavity, to enable a surgeon to concurrently use an endoscope and one or more other devices inserted into the body cavity.

An example of a known trocar is shown in U.S. Pat. No. 5,256,149 to Banik et al. This patent discloses a trocar constructed from a transparent plastic material and includes a trocar cannula with a cannula handle, a cannula tube and a trocar obturator passing through the handle and tube. The device also includes a gas inlet having a valve thereon to enable a gas to be used to insufflate and desufflate a body cavity into which the trocar cannula has been inserted and is held. After the obturator is used to pierce a person's body and form an opening into an underlying body cavity, the trocar cannula may be threaded into the opening formed into the body cavity with a stability thread to aid in securing the trocar cannula in place. The obturator is removed from the trocar cannula, and an instrument such as an endoscope, an endoscopic needle grasper, a holding device, a manipulating device, or the like, may be inserted through the trocar cannula into the body cavity.

During many types of surgery a number of trocars are inserted so that there are a number of passageways into the selected body cavity. One or more of these passageways may be used to move or position an organ if a further portion thereof must be seen or operated on. In addition, the organ may cover or block another organ which needs to be examined or operated on. This is usually accomplished by the insertion of a grasping or manipulating device or instrument, into a passageway in one of the trocars. However, the grasping or manipulating instrument is usually loosely aligned in the trocar passageway and must be held in position or somehow secured so that any organ or the like that it is pressing against or supporting, does not move or shift. Since the surgeon and/or assistant must concentrate on specific steps and requirements during a surgical procedure, and often need both of their respective hands, a holding means or another person must help to hold or support the grasping or manipulating device. Often, however, it is left to the surgeon or assistant to try to hold the instrument steady by the use of a surgical clamp between the instrument and a surgical drape on the patient, or somehow jury rig a means to hold or support the instrument. For numerous reasons, surgeons and their assistants have difficulty in fully or properly holding or supporting such instruments, and problems have occurred. Therefore, a need exists for a simple and effective means for holding a grasping or manipulating instrument in place in a trocar during surgical procedures, such as endoscopic surgery.

SUMMARY OF THE INVENTION

Accordingly, it is a general object of the present invention to provide an instrument holding means. It is a particular object of the present invention to provide an instrument holding means which is easy to manufacture and use. It is a still more particular object of the present invention to provide an instrument holding means which is readily inserted in an existing opening in a trocar. It is yet a more particular object of the present invention to provide an instrument holding means with an easily recognized enlarged head or handle, to enable the holding means to be easily inserted into and/or removed from an opening in a trocar. It is a further object of the present invention to provide an instrument holding means which has a phosphorescent handle that may easily be seen in a darkened operating room. It is yet another object of the present invention to provide a locking device having self-tapping threads, which locking device is capable of being manufactured as original equipment for a trocar, or for retrofit into an existing trocar gas inlet. And, it is yet a further object of the present invention to provide a locking device which includes coarse self-tapping threads for quick and easy insertion into, and removal from, the existing gas inlet of a trocar.

In accordance with one aspect of the present invention, there is provided a locking device for use in a trocar to hold an instrument in place. The locking device is quickly and easily inserted and held in an existing gas inlet in the trocar and includes an enlarged head that may be easily grasped and recognized by a surgeon during surgery. An elongated shaft portion is secured to the enlarged head, and the shaft is capable of being threaded into the gas opening in the trocar by turning the enlarged head. The elongated shaft has coarse, self-tapping threads formed only on an upper portion thereof, adjacent the enlarged head. The device speeds up the time it takes to insert it into position and to lock an instrument inserted into the trocar. The outer end of the elongated shaft must contain a soft surface to prevent damaging or marring the instrument which it is holding.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, in which:

FIG. 1 is a perspective view of a prior art trocar inserted into a body cavity with a grasping or manipulating instrument inserted through the trocar into the body cavity, and also showing a preferred embodiment of the locking device of the present invention, threaded into position through the trocar for holding the instrument in position and preventing movement thereof; and FIG. 2 is a partial enlarged side elevational view of the inventive locking device held in the trocar of FIG. 1, showing a portion of the trocar in cross section.

DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to describe an instrument locking means, identified generally at 10, for use in substantially any existing trocar, such as 12, or more specifically an existing gas opening 14 in the trocar 12 to hold or lock an instrument such as 16 with respect to the trocar. For reasons of explanation only, and not by way of limitation, the locking device 10 is described and shown herein for use in a specific trocar, such as described and claimed in U.S. Pat. No. 5,256,149 to Banik et al. ("'149"), having a transparent plastic body. The relevant portions of this '149 patent are incorporated herein in their entirety by this reference thereto. It is to be understood that the present invention provides a locking means for use in any existing gas opening of substantially any similar trocar or similar surgical instrument requiring a means to hold an instrument inserted therein in an immovable or locked position.

Since only one of the gas inlets of a plurality of trocars must be used to insufflate and desufflate the internal body cavity, if a plurality of trocars are inserted into a selected body cavity, one or more of the other gas inlets may be provided with a locking means 10 inserted therein.

As shown in the drawings, after a trocar 12 has been inserted through a skin layer, etc. 18, so as to be connected to an internal cavity 20 and an obturator (not shown) removed, in a manner well known to those skilled in the art, an instrument 16 is inserted through a passage 17 in the trocar. After the instrument 16 is inserted and moved, or manipulated to a preferred or selected position, the locking means 10 may be screwed down so as to lock the instrument against further movement, with respect to the trocar. This frees up the hands of a surgeon, or the surgeon's assistant, to perform the rest of the surgical procedure through one or more other trocars, not shown, in an expeditious and safe manner.

The locking means 10 has an enlarged, preferably spherical head 22 secured to an elongated shaft 24 having coarse, self-tapping threads 26 thereon. The spherical head 22 is preferably knurled, roughened or serrated to enable the locking device to be easily grasped and turned by the finger tips of a surgeon or assistant during an operation, for full insertion into an opening 23 in the gas inlet 14 by action of the self tapping threads 26, as explained below. Furthermore, the spherical head 22 is preferably made from or covered with a phosphorescent material so as to be more easily recognized under low lighting conditions that often occur during endoscopic surgery procedures.

As is disclosed in the '149 patent, the housing of the trocar, including the valve and inlet 14, are manufactured from plastic. Therefore, the locking means 10, including head 22, the shaft 24 and threads 26, are preferably formed from a metal, such as stainless steel, or other hardened plastic or metal material. As is often the case, the material may be coated or uncoated, as long as it may be easily sterilized and is approved for medical use. By using a hardened material it can be seen that the locking means 10 will be quickly turned by head 22 and that the self-tapping threads 26 will easily form internal threads in inlet opening 23. As shown in FIG. 2, the self-tapping threads 26 do not start at the lower or free end 28 of the elongated shaft, but are formed on a central or upper portion thereof, adjacent the head 22. The locking means 10 will, therefore, be quickly inserted and then turned so as to move downwardly or inwardly, into opening 23, until the lower or outer end 28 is brought into contact with the instrument 16. The lower or outer end 28 is preferably blunt and softened so that when it moves into contact with the instrument 16, it will not damage, mar or mark the same, and so that it will have a larger contact surface which will frictionally engage instrument 16, to prevent it from moving with respect to the trocar 12.

As described above, the locking means 10 of the present invention is inserted into an existing gas opening in a trocar, after the trocar is inserted into a body cavity with at least one other trocar. Locking means 10 is inserted and held in the opening so as to be readily available and accessible to a surgeon or an assistant during a surgical procedure, for tightening the same. The surgeon's or assistant's hands are thereby left free for more important tasks. Because of the size and ability of the enlarged head to be seen in a darkened operating room, the locking device may be conveniently operated in the existing opening in a trocar in critical situations without requiring any special tools, adjustments, or changes to existing equipment. Furthermore, its self-tapping screw threads, as well as the placement thereof adjacent to the head, allow it to be easily inserted and quickly operated to lock the instrument 16 in place.

Thus, it can be seen that the locking means of the present invention provides a lock that is compatible with existing trocars for easy insertion into a formed opening therein, and that it can be easily installed by a manufacturer of trocars, at the factory when assembling the trocar.

Those skilled in the art will appreciate that various adaptations and modifications of the just-described preferred embodiments can be configured without departing from the scope and spirit of the invention. Therefore, it is to be understood that, within the scope of the appended claims, the invention may be practiced other than as specifically described herein.

What I claim is:

1. A locking means for holding an instrument in a trocar inserted into a body cavity comprising, in combination:
    an enlarged head;
    an elongated shaft secured at a first end to said enlarged head and having a second soft end;
    a thread formed only a limited portion of said elongated shaft; and
    said thread being self-tapping so that it may be threaded into an unthreaded passage in said trocar by rotation of said enlarged head so as to secure the instrument in position in the trocar and extending into said body cavity, by said second soft end.

2. The locking means of claim 1 wherein said enlarged head is provided with a roughened surface to aid in the grasping thereof.

3. The locking means of claim 1 wherein said enlarged head is phosphorescent.

4. The locking means of claim 1 wherein said self-tapping thread is formed on only a proximal portion of said elongated shaft.

5. The locking means of claim 4 wherein said self-tapping thread is formed on said elongated shaft adjacent to said enlarged head.

6. The locking means of claim 5 wherein said self-tapping threads are coarse.

7. The locking means of claim 4 wherein said self-tapping thread is formed on a portion of said elongated shaft between said second soft end and said enlarged head, but closer to said enlarged head.

8. The locking means of claim 7 wherein said self-tapping threads are coarse.

9. A combination trocar and locking means for holding an instrument in a passageway formed through said trocar comprising, in combination:

a gas opening formed on said trocar; said gas opening connected to said passageway;

said locking means having an enlarged head; an elongated shaft secured at a first end to said enlarged head and having a second soft end; and a self tapping thread formed on only a limited portion of said elongated shaft; and said locking means being inserted into said gas opening in said trocar with said self tapping thread being in contact with said gas opening so that said locking means may be threaded into said gas opening by rotation of said enlarged head until said second soft end contacts said instrument in said passageway so as to prevent said instrument from moving with respect to said trocar.

10. The combination trocar and locking means of claim 9 wherein said thread on said elongated shaft is self-tapping so that said locking means may be quickly threaded into an unthreaded passage by rotation of said enlarged head.

11. The combination trocar and locking means of claim 10 wherein said self-tapping thread is formed on only a limited portion of said elongated shaft, adjacent said enlarged head.

12. The combination trocar and locking means of claim 11 wherein said self-tapping threads are coarse.

13. The locking means of claim 10 wherein said self-tapping thread is formed midway between said second soft end and said enlarged head.

14. The combination trocar and locking means of claim 13 wherein said enlarged head is roughened to aid in the grasping thereof.

15. The combination trocar and locking means of claim 14 wherein said enlarged head is phosphorescent.

16. A locking means for preventing movement of an instrument passing through a trocar, inserted into a body cavity comprising, in combination:

an enlarged knurled, phosphorescent head;

an elongated shaft having first and second ends; the first end being secured to said enlarged knurled, phosphorescent head and the second end being blunt and soft;

a self-tapping thread formed on a limited portion of said elongated shaft, adjacent to said enlarged knurled, phosphorescent head and said blunt and soft second end; and the limited portion of self-tapping thread being quickly threaded into an unthreaded passage formed in the trocar by rapid rotation of said enlarged knurled, phosphorescent head to secure an instrument passing through the trocar into said body cavity from movement with respect to said trocar by said blunt and soft second end.

\* \* \* \* \*